US012797328B2

(12) United States Patent
Rana et al.

(10) Patent No.: US 12,797,328 B2
(45) **Date of Patent: *Nov. 17, 2026**

(54) STABLE AQUEOUS INJECTABLE SOLUTION OF EPINEPHRINE

(71) Applicant: Sun Pharmaceutical Industries Limited, Mumbai (IN)

(72) Inventors: Amar Rana, Baroda (IN); Rakesh Thummar, Baroda (IN); Sudeep Agrawal, Baroda (IN); Subhas Balaram Bhowmick, Baroda (IN); Rajamannar Thennati, Baroda (IN)

(73) Assignee: SUN PHARMACEUTICAL INDUSTRIES LIMITED, Mumbai (IN)

(*) Notice: Subject to any disclaimer, the term of this patent is extended or adjusted under 35 U.S.C. 154(b) by 1382 days.

This patent is subject to a terminal disclaimer.

(21) Appl. No.: 17/443,766

(22) Filed: Jul. 27, 2021

(65) Prior Publication Data

US 2021/0353531 A1 Nov. 18, 2021

Related U.S. Application Data

(63) Continuation of application No. 16/738,147, filed on Jan. 9, 2020, now Pat. No. 11,234,925.

(30) Foreign Application Priority Data

Jan. 10, 2019 (IN) ............................ 201921001282

(51) Int. Cl.

| | |
|---|---|
| ***A61K 9/00*** | (2006.01) |
| ***A61K 9/08*** | (2006.01) |
| ***A61K 31/137*** | (2006.01) |
| ***A61K 47/10*** | (2017.01) |
| ***A61K 47/12*** | (2006.01) |
| ***A61K 47/18*** | (2017.01) |
| ***A61K 47/20*** | (2006.01) |

(52) U.S. Cl.

CPC .............. *A61K 9/0019* (2013.01); *A61K 9/08* (2013.01); *A61K 31/137* (2013.01); *A61K 47/10* (2013.01); *A61K 47/12* (2013.01); *A61K 47/183* (2013.01); *A61K 47/20* (2013.01)

(58) Field of Classification Search

None

See application file for complete search history.

(56) References Cited

U.S. PATENT DOCUMENTS

| | | | |
|---|---|---|---|
| 8,628,805 | B2 | 1/2014 | Baillie et al. |
| 9,119,876 | B1 | 9/2015 | Kannan et al. |
| 9,283,197 | B1 | 3/2016 | Taneja |
| 2014/0343159 | A1 | 11/2014 | Fahl |
| 2015/0246009 | A1 | 9/2015 | Gupta et al. |
| 2016/0058715 | A1 | 3/2016 | Rakesh et al. |
| 2016/0263059 | A1 | 9/2016 | Kannan et al. |

FOREIGN PATENT DOCUMENTS

WO WO-2014057365 A1 4/2014

OTHER PUBLICATIONS

Sacha Pollard, et al; title: Vasopressor and Inotropic Management of Patients With Septic Shock; P&T, vol. 40(7); pp. 438-442 and 449-450, published Jul. 15, 2015. (Year: 2015).

Sandoz, non-patent literature, titled: SYMJ EPI™ (epinephrine) Injection; approved by FDA on Jun. 15, 2017. tTe product information is downloaded on Mar. 6, 2020. (Year: 2017).

Search Report and Written Opinion received in International Application No. PCT/IB2020/050148 mailed Mar. 24, 2020, 11 pages.

Title: Epinephrine Concentrate Injection, Medically reviewed by Drugs.com; Last updated on Jul. 1, 2018. Downloaded from https://www .drugs.com/pro/epinephrine-concentrate-injection.html on Mar. 3, 2020 (Year: 2018).

*Primary Examiner* — Layla Soroush

(74) *Attorney, Agent, or Firm* — Blank Rome LLP

(57) ABSTRACT

The present invention provides a stable, aqueous injectable solution comprising epinephrine or its pharmaceutically acceptable salt, a sulfite antioxidant, butylated hydroxyl anisole, an organic acid and a chelating agent, wherein the solution is free of an inorganic acid and an inorganic base. The invention also provides a method of treating the septic shock by intravenous administration of stable aqueous injectable solution comprising epinephrine or its pharmaceutically acceptable salt, a sulfite antioxidant, butylated hydroxyl anisole, an organic acid and a chelating agent, wherein the solution is free of an inorganic acid and an inorganic base.

20 Claims, No Drawings

STABLE AQUEOUS INJECTABLE SOLUTION OF EPINEPHRINE

This application is a continuation of U.S. patent application Ser. No. 16/738,147, filed Jan. 9, 2020, which claims priority to Indian Application No. 201921001282 filed Jan. 10, 2019, the entire contents of which are hereby incorporated by reference herein.

FIELD OF THE INVENTION

The present invention relates to a stable aqueous injectable solution of epinephrine.

BACKGROUND OF THE INVENTION

Epinephrine, an endogenous adrenergic neurotransmitter has been available as an injectable preparation for various indications for emergency treatment of allergic reactions (Type I) including anaphylaxis. Many commercial products such as for example, Epipen®, Adrenalin®, Symjepis®, Auvi-Q® Adrenaclick® are available wherein epinephrine is present at a concentration of 0.5 mg/ml or 1 mg/ml, in volumes of 0.76 ml to 2 ml having sodium metabisulphite as an stabilizer. These products are presented as either a vial or prefilled syringe, Out of these, the most recently approved is Adrenalin® by PAR Pharmaceuticals. Adrenalin® is an aqueous solution that contains 1 mg/ml epinephrine base, sodium chloride, sodium metabisulphite, tartaric acid, disodium edetate, sodium hydroxide and hydrochloric acid pH to 2.2 to 5.0 and is provided as single dose injection solution in volume of 1 ml in a vial.

The present inventors while developing an improved stable aqueous injectable solution found that the presence of inorganic acid such as hydrochloric acid and inorganic base such as sodium hydroxide generated high, undesirable impurities. The undesirable impurities generated were epinephrine sulphate and D-epinephrine. It is known that D-epinephrine (Formula II) is less potent than L-epinephrine (Formula I), see U.S. Pat. No. 9,283,197 (hereinafter referred to as US '197).

Formula I

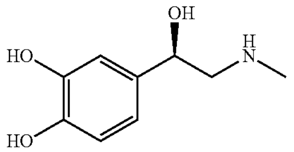

Formula II

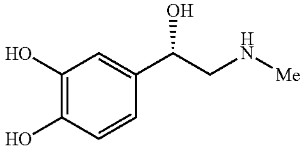

The US '197 patent describes the problem of racemization and oxidation of epinephrine to less potent D-form of epinephrine and adrenaline, a less potent ketone form which has little adrenergic activity.

SUMMARY OF THE INVENTION

The present invention provides a stable, aqueous injectable solution comprising epinephrine or its pharmaceutically acceptable salt, a sulfite antioxidant, butylated hydroxyl anisole, an organic acid and a chelating agent, wherein the solution is free of an inorganic acid and inorganic base.

The invention also provides a method of treating the septic shock by intravenous administration of stable aqueous injectable solution comprising epinephrine or its pharmaceutically acceptable salt, a sulfite antioxidant, butylated hydroxyl anisole, an organic acid and a chelating agent, wherein the solution is free of an inorganic acid and inorganic base.

DESCRIPTION OF THE INVENTION

The present invention provides a stable, aqueous injectable solution comprising epinephrine or its pharmaceutically acceptable salt, a sulfite containing antioxidant, butylated hydroxyl anisole, an organic acid and a chelating agent, wherein the solution is free of an inorganic acid and inorganic base. The said solution can be used to increase mean arterial blood pressure in adults having hypotension associated with septic shock.

The term 'stable' as used herein means that the aqueous solution of epinephrine remains physically and chemically stable at room temperature and the content of known impurities such as D-epinephrine or epinephrine sulphate is less than 0.5% when the solution is stored in a glass container or any other container impermeable to oxygen or air, at 40° C./75% relative humidity for one month. Preferably, the epinephrine sulphate is less than 1.0% when the solution is stored in a glass container or any other container impermeable to oxygen or air, at 40° C./75% relative humidity for six months.

The term 'inorganic acid' as used herein means any acid that completely dissociates in water into the anion and $H^+$ ions. For example, hydrochloric acid, nitric acid, sulphuric acid, hydrobromic acid and so on. The term 'inorganic base' herein means any base that completely dissociates in water into the cation and $OH^-$. For example, sodium hydroxide, potassium hydroxide, calcium hydroxide, lithium hydroxide and so on.

The known impurities of epinephrine include D-epinephrine and Epinephrine sulphate. The chemical structures of D-epinephrine and Epinephrine sulphate impurity are represented by Formula II and III; respectively.

Formula II

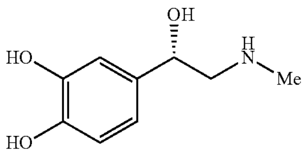

Formula III

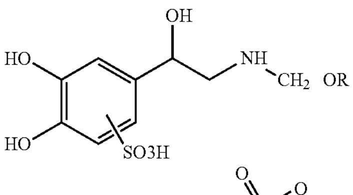

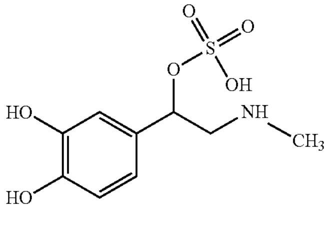

Epinephrine or its pharmaceutically acceptable salt equivalent to epinephrine base is present in the aqueous solution of the present invention in therapeutically effective amounts. Preferably, epinephrine or its pharmaceutically acceptable salt equivalent to epinephrine base is present in the aqueous solution in an amount ranging from 0.01 mg/ml to 0.5 mg/ml, such as for example, 0.01, 0.02, 0.03, 0.04, 0.05, 0.06, 0.07, 0.08, 0.09, 0.1, 0.11, 0.012, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5 mg/ml. In one particular embodiment, epinephrine or its pharmaceutically acceptable salt is present in an amount ranging from about 0.10 mg/ml to about 0.11 mg/ml.

In one embodiment, the salt of epinephrine may be any suitable salt with an organic acid. In a preferred embodiment, some of the pharmaceutically acceptable salts of epinephrine may be tartrate, bitartrate, borate citrate, etc. In a more preferred embodiment tartrate salt of epinephrine is used for the purpose of present invention.

The term 'sulfite containing antioxidant' as used herein means any anti-oxidant capable of providing sulfite, bisulfite, or metabisulfite anions in water, for instance, sodium sulphite, sodium bisulfite, sodium metabisulphite, sodium pyrosulphite and the like. The sulfite containing antioxidant may be selected from, but not limited to, sodium sulfite, sodium bisulfite or sodium metabisulfite. In one embodiment, the sulfite containing antioxidant is in the aqueous solution at a concentration ranging from 0.1 mg/ml to 0.5 mg/ml. In one preferred embodiment, the sulfite containing antioxidant used is sodium metabisulfite and it is present in the aqueous solution at a concentration of 0.17 mg/ml.

In a preferred embodiment, the aqueous solution of the present invention comprises a unique mixture of a sulfite containing antioxidant and butylated hydroxyl anisole. Butylated hydroxyl anisole (BHA) may be present in the aqueous solution according to the present invention in an amount ranging from about 0.0001 mg/ml to about 0.1 mg/ml, preferably in an amount ranging from about 0.001 mg/ml to 0.005 mg/ml. In one particularly preferred embodiment, butylated hydroxyl anisole may be present in the aqueous solution of the present invention in an amount of 0.003 mg/ml.

In one embodiment, the pH of the aqueous solution is adjusted in the desired range by an organic acid. In a preferred embodiment, the organic acid is tartaric acid. In such embodiments, the tartaric acid is present in amounts ranging from about 0.03 mg/ml to about 0.11 mg/ml, which dissolves epinephrine and forms in-situ epinephrine tartrate salt. In a preferred embodiment, the stable, aqueous injectable solution of the present invention is free of an inorganic acid such as hydrochloric acid and an inorganic base such as sodium hydroxide. In such preferred embodiments of the invention, the said solution has a pH in the range of 3.4 to 4.5. In a more preferred embodiment, the stable, aqueous injectable solution of the present invention has a pH in the range of 3.8±0.3. The aqueous solution is free of any buffer, which is a couple of an inorganic acid and an inorganic base or salt along with an inorganic acid or an inorganic base.

The stable, aqueous injectable solution of the present invention further comprises a chelating agent. The chelating agent that may be used in the present invention may be selected from, but not limited to, disodium edetate, disodium edetate dihydrate, ethylenediamine tertaacetic acid, diaminoethane tetraacetic acid and the like or mixture thereof. The chelating agent may be present in the aqueous solution in an amount ranging from about 0.05 mg/ml to about 2.0 mg/ml. In a preferred embodiment, disodium edetate dihydrate is used as a chelating agent and is present in the aqueous solution in an amount ranging from 0.1 mg/ml to 0.3 mg/ml. In a more preferred embodiment, disodium edetate dihydrate is present in the aqueous solution in an amount of 0.2 mg/ml.

The stable, aqueous injectable solution may further comprise other parenterally acceptable excipients. The aqueous solution of the present invention may comprise an osmotic agent or tonicity adjusting agent, in suitable amounts to adjust the osmolality of the solution in the range of about 250-375 mOsm/kg, preferably 270-330 mOsm/kg. The osmotic agent that may be used in the present invention may be selected from, but not limited to, sodium chloride, potassium chloride, calcium chloride, mannitol, glycerol, sorbitol, propylene glycol, dextrose, sucrose, and the like and mixtures thereof. According to one preferred embodiment, the osmotic agent is sodium chloride and it may be used in the solution in an amount ranging from about 5 mg/ml to 9 mg/ml. In the most preferred embodiment, the stable, aqueous injectable solution is free of any inorganic acid and inorganic base.

The stable, aqueous injectable solution of the present invention comprises a pharmaceutically acceptable solvent such as water for injection. Preferably according to one embodiment of the present invention, the stable, aqueous injectable solution of the present invention is free of co-solvents such as alcohols or glycols.

The volume of the stable, aqueous injectable solution filled in the container ranges from about 10 ml to 200 ml, preferably 10 ml to 100 ml, more preferably, 10 ml to 50 ml, such as for example 20, 30, 40 or 50 ml. According to a preferred embodiment, the volume of aqueous solution of epinephrine filled in the container is about 10 ml.

In one embodiment of the present invention, the stable, aqueous injectable solution of epinephrine is filled in a container selected from a prefilled syringe, autoinjector, vial or ampoule. In a preferred embodiment, the container is a prefilled syringe. In another preferred embodiment, the container is an autoinjector. More preferably, the stable, aqueous injectable solution is filled into prefilled glass syringe which can be directly attached to an infusion bag. When the container is a prefilled syringe or an autoinjector, the barrel is made up of an impermeable material such as glass. Preferably, the barrel is made up of USP Type I siliconized glass. In another embodiment, the barrel is made up of a non-glass polymeric material selected from cycloolefin polymer, cycloolefin copolymer, polyolefins polycarbonates, styrene-polyolefin based polymers and block co-polymers thereof. The barrel is sealed at one end with a plunger which has a stopper or stopper valve. According to one embodiment, the plunger stopper or the valve is made up of a non-glass component. In one embodiment, the stopper or the valve is made up of a non-glass, rubber, elastomeric material, preferably a thermoplastic elastomer, but may also be made up of other suitable material such as high density polyethylene or low density polyethylene. The rubber or elastomeric material may include, but is not limited to bromobutyl rubber, chlorobutyl rubber, styrene butadiene rubber and the like. Preferably, the tip cap is made up of USP type II rubber. In one preferred embodiment the plunger stopper is made up of bromobutyl rubber which is in direct contact with the aqueous injectable solution comprising epinephrine or its pharmaceutically acceptable salt in an amount ranging from about 0.05 mg/ml to about 0.15 mg/ml, a sulfite antioxidant, butylated hydroxyl anisole, tartaric acid and a chelating agent, wherein the solution is free of an inorganic acid and an inorganic base, e and wherein the pH of the solution ranges from 3.4 to 4.5. In one of the most preferred embodiment, pH of the solution is in the range of 3.8±0.3. It was found that the impurity, epinephrine sulphate is less than 1.0% when the solution is stored in an impermeable container as above at 40° C./75% relative humidity for six months compared to 1.7% of epinephrine sulphate in which an inorganic acid and an inorganic base was added to adjust the pH to 3.8±0.3.

The container-closure components of the prefilled syringe comprise various potential leachables and extractables. The tip cap component of prefilled syringe includes phenolic antioxidants, low molecular weight polymer, butylated hydroxyl toluene, palmitate/stearate, magnesium and zinc ion as potential extractables. Said syringe includes potential extractables such as silicone oxide, boron oxide, aluminium oxide, sodium oxide, barium oxide, calcium oxide. The rubber plunger stopper includes potential extractable such as low molecular weight polymer, palmitate/stearate, residual solvents, magnesium, and zinc ion and so on. The stable, aqueous injectable solution of epinephrine was found to be free of extractables and leachables.

In one embodiment, the device may be enclosed in a secondary packaging that stores the container having the injectable aqueous solution of epinephrine. The secondary packaging may be an aluminium pouch, blisters and/or a carton which may be opaque or transparent or opaque with a window. Additionally, a suitable oxygen scavenger may be included inside the secondary packaging. In a preferred embodiment, container filled with the aqueous injectable solution of epinephrine is supplied in carton. The carton includes a partition to carry the components of the container, namely needle, barrel or autoinjector other parts.

The stable, aqueous injectable solution of the present invention may have oxygen content of less than 2 ppm, more preferably less than 1 ppm. Preferably, the aqueous solution of the present invention is prepared by a process wherein the oxygen levels are maintained to be less than 2 ppm, more preferably less than 1 ppm. The process may include steps of purging of an inert gas such as nitrogen or argon while preparing the solution or after the solution is prepared.

In the present invention, the stable aqueous injectable solution of epinephrine can be filled in pre-filled syringe which can be readily attached to the infusion bag. This provides rapid fluid resuscitation as well as increasing the mean arterial pressure to the patient saving time. The stable, aqueous injectable solution of the present invention is suitable for administration by intravenous route only and not suitable for subcutaneous or intramuscular route of administration.

According to another aspect, the present invention provides a method of treating the septic shock by intravenous administration of stable aqueous injectable solution comprising epinephrine or its pharmaceutically acceptable salt, a sulfite antioxidant, butylated hydroxyl anisole, tartaric acid and a chelating agent, wherein the solution is free of an inorganic acid and inorganic base. In a preferred embodiment the solution comprises epinephrine in an amount ranging from about 0.05 mg/ml to about 0.15 mg/ml. The method as provided herein is useful to increase in the mean arterial blood pressure in patients with hypotension associated with septic shock. More particularly, the method comprises adding 10 ml of the stable, aqueous injectable solution comprising epinephrine or its pharmaceutically acceptable salt in an amount ranging from about 0.05 mg/ml to about 0.15 mg/ml, a sulfite antioxidant, butylated hydroxyl anisole, tartaric acid and a chelating agent, wherein the solution is free of an inorganic acid such as hydrochloric acid and inorganic base such as sodium hydroxide, and wherein the pH of the solution ranges from 3.4 to 4.5. In one of the most preferred embodiments, pH of the solution ranges from 3.8±0.3 and is added to 1000 ml of 5% w/v dextrose solution and the solution is infused into a large vein, while avoiding the use of catheter tie-in technique.

In one specific embodiment of the method, the infusion rate of the intravenous administration of epinephrine is 0.05 mcg/kg/min to 2 mcg/kg/min and is titrated to achieve a desired mean arterial pressure and the dosage is adjusted periodically such as every 10 to 15 minutes in increments of 0.05 mcg/kg/min to 0.2 mcg/kg/min, wherein the infusion is given for few hours to days until the patient's hemodynamic status is improved. In the method, the infusion rate of the intravenous administration of epinephrine is 0.05 mcg/kg/min to 2 mcg/kg/min and is titrated to achieve a desired mean arterial pressure and the dosage is adjusted periodically such as every 10 to 15 minutes in increments of 0.05 mcg/kg/min to 0.2 mcg/kg/min, wherein the infusion is given for few hours to days until the patient's hemodynamic status is improved and then after hemodynamic stabilization, doses of epinephrine are decreased every 30 minutes over a 12 to 24 hour period.

In a preferred embodiment, epinephrine is administered to the patients by adding 10 ml of epinephrine (1 mg) using a prefilled syringe to 1000 ml of 5 percent dextrose containing solution wherein each ml of this dilution contains 1 μg of epinephrine used to increase mean arterial blood pressure in adults with hypotension associated with septic shock.

Hereinafter, the invention will be more specifically described by way of Examples. The examples are not intended to limit the scope of the invention and are merely used as illustrations.

Comparative Example and Example 1

TABLE 1

Comparative example and Example 1 of present invention

| Ingredients | Comparative Example mg/ml | Comparative Example % w/v | Example 1 of present invention mg/ml | Example 1 of present invention % w/v |
|---|---|---|---|---|
| Epinephrine | 0.11 | 0.011 | 0.11 | 0.011 |
| Tartaric acid | 0.11 | 0.011 | 0.1 | 0.011 |
| Sodium metabisulphite | 0.17 | 0.017 | 0.17 | 0.017 |
| Sodium chloride | 9 | 0.9 | 9 | 0.9 |
| Butylated hydroxyl anisole | 0.003 | 0.0003 | 0.003 | 0.0003 |
| Disodium edetate | 0.2 | 0.02 | 0.2 | 0.02 |
| Hydrochloric acid (4% w/v solution) | 1.32 | 0.132 | — | — |
| Sodium hydroxide | q.s | | — | — |
| Water for injection | q.s to 1 ml | | q.s to 1 ml | |
| pH | 4.0 | | 3.85 | |

Method of Preparation—Comparative Example: Water for injection was taken in a glass vessel and nitrogen was purged continuously into it to achieve and maintain dissolved oxygen level below 1 ppm. The solution was cooled to 2-8° C. Weighed amounts of butylated hydroxyl anisole, disodium edetate, sodium chloride, epinephrine, hydrochloric acid, and sodium metabisulphite were added to the above vessel with stirring and continuous purging of nitrogen. pH was adjusted to about 4.0 using 1% w/v solution of sodium hydroxide and hydrochloric acid with continuous nitrogen purging. Volume was made up using water for injection. The solution was filtered through 0.2 micron PVDF capsule filter. The 10 ml of filtered solution was filled into a cartridge having a standard fill volume of 10.5 ml. The filled cartridges were stoppered with plungers. The prefilled syringe was placed in polyethylene bag. The polyethylene bag containing prefilled syringe was placed in corrugated box.

Method of Preparation for Example 1: Water for injection was taken in a glass vessel and nitrogen was purged continuously into it to achieve and maintain dissolved oxygen level below 1 ppm. The solution was cooled to 2-8° C. Weighed amounts of butylated hydroxyl anisole, disodium edetate, sodium chloride, tartaric acid, epinephrine and sodium metabisulphite were added to the above vessel with stirring and continuous purging of nitrogen. Volume was made up using water for injection. The solution was filtered through 0.2 micron PVDF capsule filter. The 10 ml of filtered solution was filled into a cartridge having a standard fill volume of 10.5 ml. The pH of the solution was about 3.85. The filled cartridges were stoppered with plungers. The prefilled syringe was placed in polyethylene bag. The polyethylene bag containing prefilled syringe was placed in corrugated box.

Example 2

The stable, aqueous injectable solution of epinephrine of Comparative example and Example 1 filled in prefilled syringes placed in polyethylene bag placed in corrugated box were stored at 40° C./75% relative humidity. The solutions were evaluated for chemical stability at 1 M, 3 M and 6M time points. These analytes were measured by standard analytical procedure. The results are given below in Table 2.

Example 3

The stable, aqueous injectable solutions of epinephrine of Comparative example and Example 1 filled in prefilled syringes were packed in aluminum pouches containing an oxygen scavenger and placed in corrugated box and were stored at 40° C./75% relative humidity. The solutions were evaluated for chemical stability at 1 M, 3 M and 6M time points. These analytes were measured by standard analytical procedure. The results are given below in Table 2.

TABLE 2

Stability data of Comparative Example and Example of the invention

| | Increase in impurity | 40° C./75% relative humidity | | | |
|---|---|---|---|---|---|
| Example No. | levels from initial | 1 M* | 2 M | 3 M | 6 M |
| Comparative Example | D-epinephrine | 0.37 | 0.78 | 1.17 | 2.30 |
| | Epinephrine sulphate | 0.50 | 0.81 | 1.03 | 1.70 |
| Example of the present invention | D-epinephrine | 0.28 | 0.49 | 1.02 | 2.10 |
| | Epinephrine sulphate | 0.12 | 0.37 | 0.63 | 0.90 |
| Example of the present invention (Packed in aluminium pouch and oxygen scavanger) | D-epinephrine | 0.068 | — | 0.655 | 1.79 |
| | Epinephrine sulphate | 0.139 | — | 0.354 | 0.477 |

M*—month

From the stability data, it can be concluded that there occurred minimal changes in the level of impurities (sulfate impurity and D-epinephrine) in case of the solution according to the present invention, while in case of comparative example, there occurred substantial increase in impurity levels upon storage. In the comparative example, the presence of inorganic acid was found to cause the increase in the known impurities such as D-epinephrine and Epinephrine sulphate. The stability results indicated that the aqueous solution of Comparative example having hydrochloric acid; an inorganic acid for pH adjustment, showed (more than 0.5%) of D-epinephrine and Epinephrine sulphate impurities just in two month when stored at 40° C./75% RH. From the above stability data, it is also seen that formation of D-epinephrine and Epinephrine sulphate is further controlled when the proposed product is stored in an aluminium pouch containing an oxygen scavenger.

Example 4

The stable, aqueous injectable solutions of epinephrine of Example 1 filled in prefilled syringes were packed in aluminum pouches containing an oxygen scavenger and placed in corrugated box and were stored at Table 3 below. The analytes were measured by standard analytical procedures. The results are given below in Table 3.

| | Description * | Assay of Epinephrine (R-Isomer) 90.0-115.0% | Assay of Sodium Metabisulfite NLT 0.017 mg/ml | Assay of BHA NLT 20% | Known impurities: Epinephrine Sulfonic acid impurity NMT 15.0% | Known impurities: Adrenalone NMT 1.0% | Known impurities: Norepinephrine NMT 1.0% | Known impurities: Impurity at RRT 0.06 NMT 4.0% |
|---|---|---|---|---|---|---|---|---|
| Initial | * | 111.31 | 0.166 | 73.71 | 0.177 | 0.004 | ND | 0.062 |
| Stage: 25° C./60% RH (Long term stability condition) | | | | | | | | |
| 1 M | * | 111.24 | 0.166 | 68.7 | 0.482 | 0.011 | ND | 0.104 |
| 3 M | * | 108.02 | 0.171 | 60.78 | 1.085 | 0.007 | 0.004 | 0.103 |
| 6 M | * | 108.08 | 0.154 | 52.64 | 2.017 | 0.016 | ND | 0.193 |
| 9 M | * | 106.77 | 0.15 | 48.02 | 2.925 | 0.021 | ND | 0.26 |
| 12 M | * | 107.47 | 0.144 | 45.51 | 3.846 | 0.022 | 0.003 | 0.289 |
| Stage: 30° C./65% RH (Intermediate stability condition) | | | | | | | | |
| 1 M | * | 111.15 | 0.167 | 66.09 | 0.748 | 0.014 | ND | 0.071 |
| 3 M | * | 107.76 | 0.166 | 55.12 | 2.022 | 0.028 | ND | 0.271 |
| 6 M | * | 106.23 | 0.146 | 43.46 | 3.768 | 0.029 | ND | 0.376 |
| 9 M | * | 104.67 | 0.146 | 41.36 | 5.625 | 0.024 | ND | 0.382 |
| 12 M | * | 104.1 | 0.134 | 37.43 | 7.51 | 0.03 | 0.004 | 0.421 |
| Stage: 40° C./75% RH (Accelerated stability condition) | | | | | | | | |
| 1 M | * | 107.65 | 0.154 | 58.67 | 2.647 | 0.026 | ND | 0.294 |
| 3 M | * | 101.27 | 0.152 | 46.08 | 7.63 | 0.041 | 0.006 | 0.491 |
| 6 M | * | 95.74 | 0.135 | 34.61 | 13.004 | 0.045 | ND | 0.702 |

| | Unknown Impurities Individual unspecified impurity NMT 0.5% | Content of S-Isomer NMT 10.0% | Total Impurities NMT 20.0% | pH 3.0-4.5 | Osmolality 270-330 mOsm/Kg | Particulate matter: Particles ≥10 μm NMT 6000 per container | Particulate matter: Particles ≥25 μm NMT 600 per container | Color and clarity ** |
|---|---|---|---|---|---|---|---|---|
| Initial | 0.037 | 0.149 | 0.526 | 3.79 | 293 | 26.67 | 0.00 | @ |
| Stage: 25° C./60% RH (Long term stability condition) | | | | | | | | |
| 1 M | 0.091 | 0.19 | 1.066 | 3.77 | 296 | 24.00 | 0.0 | @ |
| 3 M | 0.082 | 0.189 | 1.729 | 3.74 | 292 | 9.33 | 0.0 | @ |
| 6 M | 0.146 | 0.285 | 2.909 | 3.78 | 295 | 48.00 | 7.33 | @ |
| 9 M | 0.182 | 0.398 | 4.087 | 3.69 | 294 | 98.67 | 4.00 | @ |
| 12 M | 0.194 | 0.566 | 5.146 | 3.52 | 294 | 112.0 | 5.33 | @ |
| Stage: 30° C./65% RH (Intermediate stability condition) | | | | | | | | |
| 1 M | 0.067 | 0.229 | 1.263 | 3.74 | 295 | 36.00 | 1.33 | @ |
| 3 M | 0.164 | 0.302 | 3.09 | 3.69 | 291 | 26.67 | 3.33 | @ |
| 6 M | 0.237 | 0.554 | 5.25 | 3.73 | 295 | 35.33 | 4.67 | @ |
| 9 M | 0.205 | 0.82 | 7.311 | 3.70 | 295 | 151.33 | 14.67 | @ |
| 12 M | 0.222 | 1.22 | 9.599 | 3.56 | 294 | 286.67 | 25.33 | @ |
| Stage: 40° C./75% RH (Accelerated stability condition) | | | | | | | | |
| 1 M | 0.194 | 0.573 | 4.02 | 3.68 | 295 | 40.67 | 8.00 | @ |
| 3 M | 0.259 | 1.37 | 10.205 | 3.70 | 291 | 227.33 | 16.67 | @ |
| 6 M | 0.279 | 2.568 | 16.909 | 3.78 | 295 | 166.67 | 2.67 | @ |

* Prefilled glass syringe contains clear colorless solution free from visible particulate matter. (Syringes are packed in Aluminum pouches with Oxygen scavenger).

** It is not pinkish and it contains no precipitation when the test solution is examined visually in a suitable clear glass test tube against a white background. If any yellow color is observed in the test solution, the absorbance of the test solution at 460 nm does not exceed that of the standard solution.

@- It is not pinkish and it contains no precipitation when the test solution is examined visually in a suitable clear glass test tube against a white background.

We claim:

1. A stable, aqueous injectable solution comprising:

epinephrine or a pharmaceutically acceptable salt thereof in an amount ranging from about 0.05 mg/ml to about 0.15 mg/ml, equivalent to epinephrine base, a sulfite antioxidant, butylated hydroxyl anisole, tartaric acid, and a chelating agent, wherein the solution is free of inorganic acid and inorganic base other than the sulfite antioxidant and wherein the pH of the solution is in the range of 3.8±0.3.

2. The stable, aqueous injectable solution as claimed in claim 1, wherein the amount of epinephrine or pharmaceutically acceptable salt thereof is 0.11 mg/ml, equivalent to epinephrine base.

3. The stable, aqueous injectable solution as claimed in claim 1, wherein the sulfite antioxidant is present in an amount ranging from about 0.1 mg/ml to about 0.3 mg/ml.

4. The stable, aqueous injectable solution as claimed in claim 1, wherein the chelating agent is disodium edetate dihydrate.

5. The stable, aqueous injectable solution as claimed in claim 4, wherein the disodium edetate dihydrate is present in an amount of 0.05 mg/ml to 2.0 mg/ml.

6. The stable, aqueous injectable solution as claimed in claim 1, wherein the tartaric acid is present in amount ranging from about 0.03 mg/ml to about 0.5 mg/ml.

7. The stable, aqueous injectable solution as claimed in claim 1, wherein butylated hydroxyl anisole is present in amount ranging from about 0.001 mg/ml to 0.005 mg/ml.

8. The stable, aqueous injectable solution as claimed in claim 1, wherein the solution has less than 1.0% by weight of epinephrine sulphate when the solution is stored in an impermeable container at 40° C./75% relative humidity for at least six months.

9. The stable, aqueous injectable solution as claimed in claim 1, wherein the solution is stored in a prefilled glass syringe.

10. The stable, aqueous injectable solution as claimed in claim 9, wherein the solution is further packaged in a secondary packaging comprising aluminum pouch and an oxygen scavenger.

11. A method of treating septic shock by intravenous administration of stable aqueous injectable solution of claim 1.

12. The method of treating septic shock as claimed in claim 11, wherein the method provides an increase in the mean arterial blood pressure in patients with hypotension associated with septic shock.

13. The method as claimed in claim 11, wherein the method comprises addition of about 10 ml of the aqueous solution of claim 1 to about 1000 ml of 5% w/v dextrose solution and intravenous infusion of the said solution into a large vein, while avoiding the use of catheter tie-in technique.

14. The method as claimed in claim 13, wherein the infusion rate of the intravenous administration is 0.05 mcg/kg/min to 2 mcg/kg/min and is titrated to achieve a desired mean arterial pressure and the dosage is adjusted periodically such as every 10 to 15 minutes in increments of 0.05 mcg/kg/min to 0.2 mcg/kg/min.

15. The stable, aqueous injectable solution as claimed in claim 10, wherein the solution has less than 0.5% by weight of epinephrine sulphate when the solution is stored in an impermeable container at 40° C./75% relative humidity for at least six months.

16. The stable, aqueous injectable solution as claimed in claim 1, wherein the solution has an oxygen content of 2 ppm or less.

17. The stable, aqueous injectable solution as claimed in claim 9 wherein the solution is free of co-solvents.

18. An aqueous injectable solution comprising:
about 10 ml of the solution of claim 1; and
about 1000 ml of a 5% w/v dextrose solution.

19. An aqueous injectable solution comprising:
about 10 ml of the solution of claim 17; and
about 1000 ml of a 5% w/v dextrose solution.

20. The stable, aqueous injectable solution as claimed in claim 1, wherein:
(a) the sulfite antioxidant is present in the solution in an amount ranging from about 0.1 mg/ml to about 0.3 mg/ml;
(b) butylated hydroxyl anisole is present in the solution in an amount ranging from about 0.001 mg/ml to about 0.005 mg/ml;
(c) tartaric acid is present in the solution in an amount ranging from about 0.03 mg/ml to about 0.5 mg/ml; and
(d) the chelating agent is disodium edetate dihydrate and is present in the solution in an amount ranging from about 0.05 mg/ml to about 2.0 mg/ml.

* * * * *